United States Patent [19]
Vedage et al.

[11] Patent Number: 4,960,941
[45] Date of Patent: Oct. 2, 1990

[54] HYDROGENATION OF AROMATIC AMINES TO PRODUCE THEIR RING HYDROGENATED COUNTERPARTS

[75] Inventors: Gamini A. Vedage, Bethleham; William W. Henderson; Bernard A. Toseland, both of Allentown; Michel Deeba, North Brunswick, all of N.J.

[73] Assignee: Air Products and Chemicals, Inc., Allentown, Pa.

[21] Appl. No.: 175,444

[22] Filed: Mar. 30, 1988

[51] Int. Cl.$^5$ ............................................. C07C 209/70
[52] U.S. Cl. ..................................... 564/450; 564/451
[58] Field of Search ................................. 564/450, 451

[56] References Cited

U.S. PATENT DOCUMENTS

| | | | |
|---|---|---|---|
| 2,511,028 | 6/1950 | Whitman | 260/563 |
| 2,606,924 | 8/1952 | Whitman | 260/563 |
| 2,606,925 | 8/1952 | Whitman | 260/563 |
| 2,606,928 | 8/1952 | Barkdoll | 260/563 |
| 3,155,724 | 11/1964 | Arthur | 260/563 |
| 3,347,917 | 10/1967 | Arthur | 260/563 |
| 3,591,635 | 7/1971 | Farrissey et al. | 260/563 B |
| 3,636,108 | 1/1972 | Brake | 260/563 D |
| 3,644,522 | 2/1972 | Brake et al. | 260/563 D |
| 3,679,746 | 7/1972 | Brake | 260/563 R |
| 3,697,449 | 10/1972 | Brake et al. | 252/474 |
| 3,711,550 | 1/1973 | Brake | 260/563 |
| 3,766,272 | 10/1973 | Brake | 260/563 B |
| 3,856,862 | 12/1974 | Chung et al. | 260/563 B |
| 3,959,374 | 5/1976 | Brennan | 260/563 B |
| 4,376,724 | 3/1983 | Mita et al. | 252/460 |
| 4,394,522 | 7/1983 | Allen | 564/451 |
| 4,394,523 | 7/1983 | Allen | 564/451 |
| 4,547,557 | 10/1985 | McDaniel | 526/106 |
| 4,754,070 | 6/1988 | Casey et al. | 564/451 |

FOREIGN PATENT DOCUMENTS 2630562  1/1978  Fed. Rep. of Germany .
1122609  8/1968  United Kingdom .

Primary Examiner—Glennon H. Hollrah
Assistant Examiner—P. O'Sullivan
Attorney, Agent, or Firm—Russell L. Brewer; James C. Simmons; William F. Marsh

[57] ABSTRACT

This invention relates to an improved hydrogenation process wherein aromatic amines are hydrogenated to their ring hydrogenated counterparts. These aromatic amines are presented by the formulas:

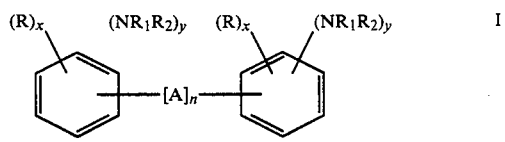

I

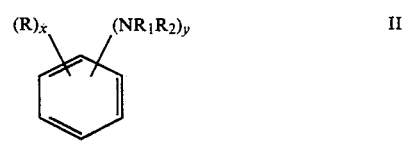

II wherein R is hydrogen or $C_{1-6}$ aliphatic, $R_1$ and $R_2$ are hydrogen or $C_{1-6}$ aliphatic, A is $C_{1-4}$, NH or

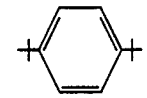

n is 0–2, x is 1–3 and y is 1 to 2 except the sum of the y groups in Formula I excluding A may be 1.

The improvement resides in the use of a rhodium catalyst carried on titania support.

29 Claims, No Drawings

HYDROGENATION OF AROMATIC AMINES TO PRODUCE THEIR RING HYDROGENATED COUNTERPARTS

TECHNICAL FIELD

This invention pertains to a process for hydrogenating aromatic amines to produce their ring hydrogenated counterparts.

BACKGROUND OF THE INVENTION

There is substantial literature in the art with respect to the hydrogenation of aromatic amines, e.g., methylenedianiline to produce 4,4'-methylenedi(cyclohexylamine), also called bis(para-aminocyclohexyl)methane, and bis(4-aminocyclohexyl)methane hereinto after referred to as PACM.

Some of the early hydrogenation work to produce PACM was done by Whitman and Barkdoll. et al. and their work is set forth in a series of U.S. Pat. Nos. 2,511,028; 2,606,924; 2,606,925; and 2,606,928. Basically the processes described in these patents involve the hydrogenation of methylenedianiline at pressures in excess of 200 psig, preferably in excess of 1,000 psig. at temperatures within a range of 80° to 275° C. utilizing a ruthenium catalyst for the hydrogenation. The hydrogenation is carried out under liquid phase conditions and an inert organic solvent is used in the hydrogenation process. Examples of ruthenium catalysts utilized for the hydrogenation process include ruthenium oxides such as ruthenium sesquioxide and ruthenium dioxide; and ruthenium salt.

Brake, et al. continued in the development of processes for manufacturing PACM by hydrogenating methylenedianiline. They found that if the ruthenium was carried upon a support and the support was alkali-moderated, the catalyst was much more active and catalytically effective in producing the desired hydrogenated PACM product. Alkali moderation was effected by contacting the catalyst and support with alkali metal hydroxide or an alkoxide; also, such alkali moderation of the catalyst could be effected prior to hydrogenation or in situ during the hydrogenation. Representative patents showing the utilization of alkali moderated ruthenium catalysts to hydrogenate methylenedianiline include U.S. Pat. Nos. 3,636,108; 3,644,522; and 3,697,449. Alkali metal and alkaline earth metal nitrates and sulfates have similarly been shown effective in U.S. Pat. No. 4,448,995 under high pressure (4000 psi) hydrogenation conditions. Representative supports in the '449 patent include bauxite, periclase, zirconia, titania, diatomaceous earth, etc.

U.S. Pat. No. 3,959,374 discloses a process for the preparation of PACM by pretreating a mixed methylenedianiline system with a nickel containing hydrogenation catalyst prior to hydrogenation with ruthenium. The pretreatment was alleged to overcome low yields (52.4%) and long reaction associated with nickel and cobalt. Ruthenium catalysts, although commonly used for hydrogenation, were not suited for hydrogenation of a feed containing impurities, e.g., isomeric impurities. Impurities in the feed allegedly caused a rapid decline in activity and hydrogenation efficiency.

U.S. Pat. Nos. 3,347,917; 3,711,550; 3,679,746; 3,155,724; 3,766,272 and British Patent No. 1,122,609 disclose various isomerization processes and hydrogenation processes to produce PACM containing high trans,trans-isomer content; i.e. an isomer content near equilibrium typically 50% trans,trans-, 43% cis,trans and 7% cis,cis-. As in the early work ruthenium catalysts were used to effect isomerization. This product was often called PACM-50.

Allen in U.S. Pat. Nos. 4,394,522 and 4,394,523 discloses processes for producing PACM by carrying out the hydrogenation of MDA in the presence of unsupported ruthenium dioxide at pressures of at least 2500 psia or in the presence of ruthenium on alumina under pressures of at least 500 psia and preferably from 1500 to 4000 psia in the presence of an aliphatic alcohol and ammonia.

Other catalysts have been utilized for the hydrogenation of methylenedianiline and examples are shown in U.S. Pat. Nos. 3,591,635 and 3,856,862. Both disclose the use of a rhodium component as a catalytic material and each require the use of an aliphatic alcohol as a solvent. The rhodium is alkali moderated using ammonium hydroxide as a pretreatment or by carrying out the reaction in the presence of ammonia. European application No. 66.212 discloses the use of rhodium on alumina to obtain 15–40% trans,transisomer ratio but again the pressures are high (4000 psi).

SUMMARY OF THE INVENTION

This invention relates to an improved process for producing aromatic amines such as 4,4'-methylenedi(cyclohexylamine) (PACM) by the catalytic hydrogenation of such aromatic amines to produce their hydrogenated counterparts. The improvement in the hydrogenation process comprises using a catalytic system comprising rhodium supported on a titania support. Preferably the catalyst comprises rhodium and ruthenium wherein the weight ratio of rhodium to ruthenium, calculated on metal content, is from 1 to 12:1.

There are several advantages associated with this process. These include:

an ability to produce a ring hydrogenated counterpart to the aromatic amine in high selectivity;

an ability to effect hydrogenation of aromatic amines at relatively low pressures e.g. 1500 psig and lower at acceptable reaction rates;

an ability to utilize an impure or crude nondistilled aromatic amine such as bridged dianilines, i.e. one containing oligomers and the formamide derivative of the dianiline as a reactant and yet obtain a hydrogenated product in high selectivity;

an ability to obtain a reaction product which is substantially free of by-product oligomers and other heavies;

an ability to eliminate alkali-moderation of the rhodium catalyst to produce the ring hydrogenated counterpart in high conversion and with excellent reaction rates; and an ability to use the catalyst for continued periods of time with only modest maintenance or regeneration techniques.

DETAILED DESCRIPTION OF THE INVENTION

This invention relates to an improvement in the conventional ring hydrogenation of aromatic amines and these amines are represented by the formulas:

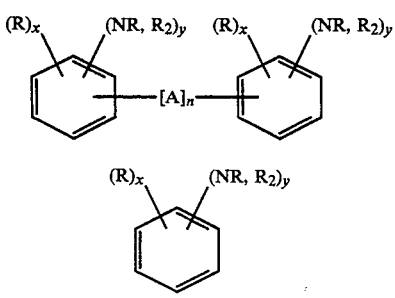

wherein R is hydrogen $C_{1-6}$ aliphatic, $R_1$ and $R_2$ are hydrogen, or $C_{1-6}$ aliphatic, A is $C_{1-4}$ alkyl, NH, or n is 0-2, x is 1-3 and y is 1-2 except the sum of the y groups in Formula I excluding A may be 1. By the practice of this invention, one is able to selectively produce a ring hydrogenated reaction product in high selectivity with excellent reaction rates. The aromatic amines useful in the practice of the process can be bridged polynuclear aromatic amines or mononuclear aromatic amines. These can be substituted with various substituents such as aliphatic groups containing from 1-6 carbon atoms. Further, the amine group can be substituted with aliphatic groups such as alkyl or alkanol groups resulting in secondary and tertiary amine substituents. Examples of bridged aromatic amines include methylene dianilines such as bis(para-aminophenyl) methane and bis(para-amino-2-methylphenyl) methane; tolidine; bis(diaminophenyl)methane; α, α-bis (4-aminophenyl-p-diisopropyl benzene(bisaniline P) bis(diaminophenyl)propane; $N-C_{1-4}$-aliphatic derivatives and $N,N'C_{1-4}$ aliphatic secondary and tertiary amine derivatives of the above bridged aromatic amines. Examples of mononuclear aromatic amines include 2,4- and 2,6-toluenediamine, aniline. butenylaniline derivatives, 1-methyl-3,5-diethyl-2,4 or 2,6-diaminobenzene (,diethyltoluenediamine,) diisopropyl-toluenediamine, tert-butyl-2,4-toluene or 2,6-diamine, cyclopent-toluenediamine, ortho-toluidine, ethyl toluidine, xylenediamine, mesitylene diamine, mono-isopropyl toluenediamine, diisopropyl toluenediamine, phenylenediamine and the N and $N,N'C_{1-4}$ aliphatic secondary and tertiary amine derivatives of the mononuclear aromatic monoamines and mononuclear aromatic diamines.

As with conventional processes the hydrogenation process is carried out under liquid phase conditions, such liquid phase conditions being maintained typically by carrying out the hydrogenation in the presence of a solvent. Although as reported in the art, it is possible to produce the reaction product in the absence of a solvent, the processing usually is much simpler when a solvent is employed. Representative solvents suited for practicing the invention include saturated aliphatic and alicyclic hydrocarbons such as cyclohexane, hexane, and cyclooctane; low molecular weight alcohols, such as methanol, ethanol, isopropanol; and aliphatic and alicyclic hydrocarbon ethers, such as n-propyl ether, isopropyl ether, n-butyl ether, amyl ether, tetrahydrofuran, dioxane, and dicyclohexylether. Tetrahydrofuran is preferred. Although in some processes water can be used as a cosolvent, it is preferred that the system be maintained in an anhydrous state or at least maintained so that the water concentration is less than 0.5% by weight. Water, when present in the system, tends to increase the amount of by-product alcohols and heavy condensation products during the hydrogenation process and tends to deactivate the catalyst system.

When a solvent is used, it can be used in concentrations as low as 50% by weight based upon the aromatic amine introduced into the reaction and typically the solvent is used at levels from about 75 to about 200% by weight of the starting compound. Under some circumstances solvent amounts as high as 1000 to 2000% based upon the weight of aromatic amine are used.

The hydrogenation is carried out principally in a batch process although it is possible to operate the plant continuously. Temperatures usually used for the hydrogenation process range from about 130° to 220° C. with preferred temperatures of from about 170° to 195° C. In the hydrogenation of MDA. when the temperature exceeds about 190° C. higher pressures and shorter reaction times are required to reduce the amount of trans,trans- isomer of PACM produced. This is particularly true where the content of the trans,trans- isomer is targeted in a range from about 17 to 24% by weight as is commercially desirable.

In contrast to the prior art hydrogenation processes particularly for bridged anilines, hydrogen partial pressures can range from about 500 to 4000 psig, preferably no higher than 2500 psig and can be as low as from about 700 to 1500 psig, which may be preferred for lower equipment and operating costs. When the pressure is raised toward the upper end of the operating range, higher reaction rates may be achieved.

The ability to ring hydrogenate aromatic amines and particularly methylenedianiline at low hydrogen partial pressures and obtain high conversion with excellent reaction rates is achieved by the utilization of a specific catalyst system. In contrast to the prior art the catalyst utilized in the hydrogenation process comprises rhodium supported on a titania support and in a preferred embodiment a mixture of rhodium and ruthenium. The ruthenium component may be present as a physical admixture carried on a support, e.g., alumina or titania or combined with the rhodium. The catalyst is particularly effective in the low pressure hydrogenation of methylene bridged aromatic amines formed by the condensation of aniline and amino and alkyl substituted anilines condensed with aldehydes, such as, formaldehyde. These bridged aromatic diamines in their undistilled state can be hydrogenated with the catalyst system whereas conventional hydrogenaton catalyst systems required purification or pretreatment of the feedstock prior to hydrogenation. The formaldehyde condensates and residues tended to poison conventional ruthenium and rhodium catalysts reducing catalytic activity or catalytic life or both.

With respect to the preferred catalyst, the rhodium to ruthenium ratio is from about 1-12, preferably 4-8 weight parts rhodium/weight part ruthenium. This catalyst system permits kinetic control of the reaction at low pressures, the ease of reaction of the mixed catalytic system being unexpectedly superior to rhodium or alone or in combination with other conventional catalysts. However, the titania support provides for enhanced results even when the rhodium component is used alone and when used with ruthenium. For example, in the hydrogenation of bridged anilines alkali-moderation of the catalyst can be eliminated.

The rhodium catalyst is combined with the titania support, based upon its weight as metal, in a ratio of about 1 to 25 weight parts rhodium per 100 weight parts of titania, preferably 3 to 8 parts rhodium per 100 parts titania. At these levels a catalyst level from 0.1 to 10% by weight of the aromatic diamine is utilized with preferred levels from 0.5 to 5% by weight. When the amount of rhodium catalyst as metal, approaches the lower limit of the range the reaction rate may decrease. However, as the concentration of rhodium increases the reaction rate will increase up to a point and then level off to a constant rate.

In the past, to maintain high activity of the catalyst system in the hydrogenation process it was proposed that the rhodium component of the catalyst be alkali moderated. Alkali moderation techniques to produce the catalyst system are well known and the techniques disclosed in U.S. Pat. No. 3,636,108 for the alkali moderation of ruthenium can be utilized for the production of rhodium. Such methods are incorporated by reference and can be done here. However, as previously noted, the titania support apparently does not need alkali metal hydroxide moderation. Typically, such alkali moderation involves the treatment of the catalyst and support material with an alkali metal hydroxide such as, sodium, lithium or potassium hydroxide or alkali metal alkoxide such as sodium, lithium, or potassium methoxide or ethoxide in an amount to provide from 0.1 to 15% by weight of a basic metal compound calculated as alkali metal. Often, alkali moderation of the catalyst is done prior to reduction of the catalyst with aqueous dilute alkali metal hydroxide during or following metal deposition on the chosen support. Alkali moderation can also be accomplished in situ during hydrogenation by including alkali metal hydroxide, e.g., lithium hydroxide, alkali metal alkoxide or by the addition of ammonia.

The progress of a hydrogenation reaction can readily be followed by observing the amount of hydrogen taken up by the reaction mixture and the reaction is terminated when the amount of hydrogen absorbed is equal or nearly equal to that amount necessary to effect complete hydrogenation of the product. In general, the hydrogenation time for aromatic amines will range from about 45 to 900 minutes, at modest catalyst levels, e.g., 0.5-5% broadly 0.1-10% by weight of the aromatic amine, and generally will not exceed 300 minutes.

The following examples are intended to illustrate various embodiments of the invention and all parts and percentages given are weight parts or weight percents unless otherwise specified.

EXAMPLE 1

Catalyst Comparison in Crude MDA Hydrogenation on Various TiO$_2$ Supports

Reaction Procedure

In this series of runs, the specified catalyst was pretreated by placing in a 300 cc autoclave with 125 g of tetrahydrofuran (THF). The sealed autoclave was purged with nitrogen followed with hydrogen and then pressurized to about 600 psig with hydrogen. The autoclave was then heated with agitation to 190° C. with addition of hydrogen as necessary to maintain a pressure of 850 psig at that temperature. After two hours, the autoclave was cooled to room temperature. After such reaction, it was believed the catalyst was fully reduced and suited for catalytic hydrogeneration.

For catalytic hydrogenation of MDA, the THF was removed from the autoclave and was replaced by the specified THF solution of a crude MDA substrate. If specified, lithium hydroxide was added as a 10% aqueous solution. The sealed autoclave was purged with nitrogen, followed with hydrogen and then pressurized to about 600 psig with hydrogen. The autoclave was then heated with agitation to the specified reaction temperature with addition of hydrogen from a ballast tank to maintain a pressure of 850 psig (a ballast tank was chosen of sufficient size and filled with hydrogen at sufficient pressure to provide all the hydrogen consumed in the reaction without dropping below 850 psig). The drop in pressure in the ballast tank provided a convenient method for observing the progress of the reaction. The reaction was considered complete when hydrogen consumption stopped. After the reaction was complete, the autoclave was cooled to room temperature, vented and the product mixture removed. The product was analyzed by capillary GC using a method previously calibrated for the materials involved. Table 1 notes reaction conditions and yield.

TABLE 1

HYDROGENATION OF METHYLENEDIANILINE

| | Catalyst | | | THF | Substrate | LiOH | Temp | Time (min) | | Yield |
|---|---|---|---|---|---|---|---|---|---|---|
| Run # | Rh/g | Ru/g | Rh/Ru | g | g | mg | °C. | Induct | Total | % |
| 1 | .73 | .18 | 4/1 | 72.5 | 52.5 | 9 | 192 | 10 | 210 | 86 |
| 2 | .73 | .09 | 8/1 | 72.5 | 52.5 | 8 | 192 | 20 | 220 | 84 |
| 3 | .73* | .09 | 8/1 | 72.5 | 52.5 | 0 | 192 | 60 | 240 | 91 |
| 4 | .58* | .24 | 2.4/1 | 72.5 | 52.5 | 0 | 192 | 30 | 200 | 91 |
| 5 | .73* | .18 | 4/1 | 72.5 | 52.5 | 0 | 192 | 35 | 205 | 96 |
| 6 | .73** | .18 | 4/1 | 72.5 | 52.5 | 0 | 192 | 0 | 50 | 90 |
| 7 | .36** | .16 | 2.25/1 | 72.5 | 52.5 | 0 | 192 | 0 | 90 | 86 |
| 8 | .36** | 0 | — | 72.5 | 52.5 | 0 | 192 | 0 | 85 | 85 |
| 9 | .21** | .16 | 1.3/1 | 72.5 | 52.5 | 0 | 192 | 0 | 130 | 86 |
| 10 | .21** | 0 | — | 72.5 | 52.5 | 0 | 192 | 0 | 140 | 85 |
| 11 | .36** | 0 | — | 72.5 | 52.5 | 0 | 160 | 60 | 344 | 89 |
| 12 | .36+ | 0 | — | 72.5 | 52.5 | 0 | 192 | 0 | 80 | 89 |
| 13 | .73++ | .11 | 6.6/1 | 72.5 | 52.5 | 0 | 192 | 0 | 95 | 82 |
| 14 | .73++ | 0 | — | 72.5 | 52.5 | — | 192 | 0 | 90 | 80 |

TABLE 1-continued

| | HYDROGENATION OF METHYLENEDIANILINE | | | | | | | | | |
|---|---|---|---|---|---|---|---|---|---|---|
| | Catalyst | | | THF | Substrate | LiOH | Temp | Time (min) | | Yield |
| Run # | Rh/g | Ru/g | Rh/Ru | g | g | mg | °C. | Induct | Total | % |
| 15 | .73+++ | 0 | — | 72.5 | 52.5 | 0 | 192 | 0 | 135 | 71 |

\*5% Rhodium on titania, Engelhard Cat #3823003
\*\*5% Rhodium on titania, Engelhard Lot #15470-4-3
+5% Rhodium on titania, Engelhard Lot #15662-41
++5% Rhodium on titania
+++5% Rhodium on titania.
Catalysts for Runs 1 and 2 were 5% metal on alumina commercially available from Engelhard. The ruthenium component of all catalyst systems consisted of 5% ruthenium on alumina.

Runs 1 and 2 show typical performance with the catalyst system of a mixture of rhodium and ruthenium both supported on alumina for hydrogenating crude MDA. Note that typically there was an induction period during the start of the reaction when little hydrogen uptake occurred. As shown in the prior art addition of lithium hydroxide was preferred to provide high yields of the desired product.

Runs 3 to 5 show the performance when the rhodium supported on alumina was replaced with rhodium on titania. This catalyst was purchased from Engelhard Corp. identified as Catalog No. 3823003. Similar total reaction times to that of Runs 1 and 2 resulted at equivalent catalyst loadings despite the longer induction periods experienced when this rhodium catalyst was used. However, exceptional yields were seen without the addition of lithium hydroxide. This particular form of titania support, however, physically degraded into finer particles thus the separation of catalyst from product was difficult.

Runs 6 to 11 show the performance with a rhodium supported on titania supplied by Engelhard Corp. (identified as lot #15470-4-3). Run 6 versus run 1 (Rh/alumina) and run 5 {Rh/titania) demonstrate the striking advantages of the rhodium catalyst supported on titania. The total reaction time was reduced by over 75% and no induction period was seen. As with Runs 3-5, the Rh/titania catalyst resulted in high yields without the addition of lithium hydroxide. Runs 7 and 9 further show the remarkable activity advantage of this catalyst at lower catalyst loadings. Runs 8 and 10 demonstrate that this $Rh/TiO_2$ catalyst is effective with crude MDA without the need for the ruthenium component in the catalyst system. An induction period was seen (run 11) after a major drop in reaction temperature, lower catalyst loading and without addition of the ruthenium component. Run 12 was identical to run 8 but with a second batch (lot #15662-41) of catalyst supplied by Engelhard.

Runs 13 to 15 further illustrate the advantages of rhodium supported on titania. These catalysts were prepared by depositing rhodium on a titania support which had been treated previously with a silica sols to improve their mechanical strength. Again, remarkable activity was seen and addition of ruthenium was not necessary to avoid an induction period.

The reasons for the improved performance with a titania support for rhodium are not fully understood. It is believed the improvement is due to at least two factors, its more inert nature and a more advantageous pore size distribution.

EXAMPLE 2

Hydrogenation of ortho-toluidine

A 30% by weight percent solution of ortho-toluidine in tetrahydrofuran was charged to a 300 cc autoclave similar to that described in Example 1. A catalyst consisting of 5% rhodium on titania, was charged to the reactor in an amount to provide 1.5 wt.% catalyst by weight of the ortho-toluidine. After purging, the reactor was pressurized to 850 psig with hydrogen and the contents heated to temperature of 170° C. After a reaction time of 240 minutes, approximately 96% of the ortho-toluidine was converted. When the above procedure was repeated but the ortho-toluidine exposed to air, catalyst activity was diminished (8% conversion in 300 min.). It was concluded that ortho-toluidine is air sensitive and the resulting oxidized product is a poison to rhodium.

EXAMPLE 3

Hydrogenation of tert-butyl-toluenediamine

The procedure of Example 2 was repeated except that tert-butyl-toluenediamine in a ratio of 80% of the isomer and 20% of the 2.6isomer was used in place of the ortho-toluidine. The catalyst comprised 0.73 grams of 5% rhodium on titania. Approximately 52 grams of tert-butyl-toluenediamine was dispersed in 72 grams tetrahydrofuran. Hydrogenation was maintained at a temperature of 192° C. at a pressure of 850 psig. The reaction time was 130 minutes and a yield of 59% hydrogenated product was obtained, thus showing the effectiveness of the catalyst for hydrogenating a mononuclear aromatic diamine.

EXAMPLE 4

Hydrogenation of 4 4'-(diaminodiphenyl) propane [bisaniline A]

The procedure of Example 3 was repeated except that 50 grams of bis aniline A were dispersed in 75 grams tetrahydrofuran. After pressurization to 850 psig with hydrogen, the contents were heated to 182° C. After reaction time of 300 minutes. 90% of the product was hydrogenated.

EXAMPLE 5

The procedure of Example 1 was repeated, except that the bottoms, which was a residue from the distillation of PACM and constituting essentially incompletely hydrogenated material resulting from the hydrogenation of crude MDA as in Example 1, was substituted for crude MDA. In one embodiment, 30 grams of a catalyst consisting of 5% rhodium on titania, as obtained from Engelhard, was dispersed in a solution of 2,000 grams PACM bottoms and 3,000 grams tetrahydrofuran. No lithium hydroxide was used to activate the catalyst. The reaction was carried out at a temperature of 180° C. for a period of 180 minutes. No induction time was observed. The percent yield based on the amine to be hydrogenated was 78%.

The above procedure was repeated, except that 120 grams of a catalyst consisting of 5% rhodium on alumina, was substituted for the catalyst consisting of rhodium on titania. In addition, 2400 mg of lithium hydroxide were added to activate the catalyst. The reaction was carried out at a temperature of 180° C. for 180 minutes. The percent yield was 80%.

From these two runs, it can be seen that the rhodium on titania catalyst system was about 4 times as active as the rhodium on alumina catalyst system. In other words, it was necessary to increase the rhodium on alumina catalyst fourfold to match the activity of the rhodium on titania.

We claim:

1. In a process for the catalytic hydrogenation of aromatic amines to their ring hydrogenated counterparts by contacting the aromatic amine with hydrogen in the presence of a rhodium catalyst, the improvement which comprises effecting said hydrogenation with a catalyst comprising rhodium supported on titania wherein the aromatic amine is represented by the formulas:

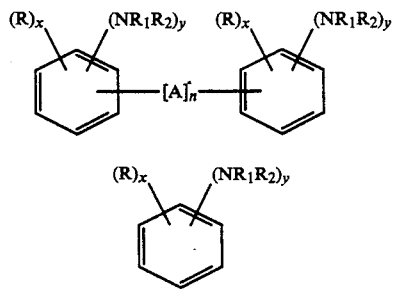

wherein R is hydrogen or $C_{1-6}$ aliphatic, $R_1$ and $R_2$ are hydrogen or $C_{1-6}$ aliphatic, A is $C_{1-4}$, NH or

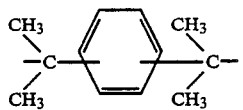

n is 0–2, x is 1–3 and y is 1 to 2 except the sum of the y groups in Formula I may be 1.

2. The process of claim 1 wherein said aromatic amine is represented by formula I.

3. The process of claim 2 wherein hydrogenation is conducted at a hydrogen pressure from about 500 to 4,000 psig.

4. The process of claim 3 wherein the catalyst is present in an amount from about 0.1 to 10% by weight of the aromatic amine.

5. The process of claim 4 wherein the percent rhodium on titania ranges from about 1 to 25 parts by weight, as metal, per 100 parts titania.

6. The process of claim 5 wherein $R_1$ and $R_2$ are hydrogen.

7. The process of claim 6 wherein R is H or methyl.

8. The process of claim 6 wherein n is 0.

9. The process of claim 6 wherein A is $CH_2$ and n is 1.

10. The process of claim 9 wherein each y is 1.

11. The process of claim 9 wherein the temperature of the reaction is within a range from about 130° to 220° C.

12. The process of claim 10 wherein the reaction is carried out in the presence of an organic solvent.

13. The process of claim 10 wherein ruthenium is added as a co-catalyst to the hydrogenation process and the ratio of rhodium to ruthenium, as metal, is from about 1–12 weight parts rhodium per weight part ruthenium.

14. In a process for the catalytic hydrogenation of 4,4' methylenedianiline containing oligomers and the formamide derivative of the dianiline to bis (4-aminocyclohexyl)methane, which comprises hydrogenating the 4,4' methylenedianiline in the presence of a catalyst system comprising rhodium, the improvement which comprises effecting said hydrogenation in the presence of a catalyst comprising rhodium supported on titania.

15. The process of the claim 14 wherein the hydrogenation is carried out at a temperature from about 130° to 220° C. a hydrogenation pressure of from about 500 to 2500 psig and for a time sufficient to effect hydrogenation of said 4,4' methylenedianiline, but for a time not to exceed about 300 minutes.

16. The process of claim 15 wherein in the pressure is from about 700 to 500 psig.

17. The process of claim 14 wherein the catalyst system comprises rhodium and ruthenium and the amount of rhodium is from 4 to 8 weight parts/weight part ruthenium, and the amount of catalyst based on methylenedianiline is from 0.5 to 5% by weight.

18. The process of claim 1 wherein said aromatic amine is represented by Formula II.

19. The process of claim 18 wherein hydrogenation is conducted at a hydrogen pressure from about 500 to 4,000 psig.

20. The process of claim 19 wherein the catalyst is present in an amount from about 0.5 to 5% by weight of the aromatic amine.

21. The process of claim 20 wherein the percent rhodium on titania ranges from about 1 to about 25 parts by weight, as metal, per 100 weight parts titania.

22. The process of claim 21 wherein $R_1$ and $R_2$ are hydrogen.

23. The process of claim 22 wherein R is methyl, ethyl, or tert-butyl.

24. The process of claim 23 wherein x is 1–2 and y is 1.

25. The process of claim 24 wherein the temperature of the reaction is within a range from about 130° to 220° C.

26. The process of claim 25 wherein the reaction is carried out in the presence of an organic solvent.

27. The process of claim 23 wherein ruthenium is added as a co-catalyst to the hydrogenation process and the ratio of rhodium to ruthenium, as metal, is from about 1–12 weight parts rhodium per weight part ruthenium.

28. The process of claim 21 wherein said aromatic amine is tert-butyl-2,4-toluenediamine or tert-butyl-2,6-toluenediamine.

29. The process of claim 21 wherein said aromatic amine is 1-methyl-3,5-diethyl-2,4- or 2,6-diaminobenzene.

* * * * *